(12) United States Patent
Solomon

(10) Patent No.: US 8,015,723 B2
(45) Date of Patent: Sep. 13, 2011

(54) DEVICE FOR MEASURING HEIGHT

(76) Inventor: Charles G. Solomon, Auburn, AL (US)

( * ) Notice: Subject to any disclaimer, the term of this patent is extended or adjusted under 35 U.S.C. 154(b) by 182 days.

(21) Appl. No.: 12/500,391

(22) Filed: Jul. 9, 2009

(65) Prior Publication Data

US 2011/0005094 A1 Jan. 13, 2011

(51) Int. Cl.
*G01B 3/02* (2006.01)
*G01B 3/04* (2006.01)

(52) U.S. Cl. ............... 33/809; 33/493; 33/512

(58) Field of Classification Search ............ 33/406, 33/458, 483, 484, 490, 493, 494, 512, 679.1, 33/719, 809; D10/70, 71
See application file for complete search history.

(56) References Cited

U.S. PATENT DOCUMENTS

| | | | | |
|---|---|---|---|---|
| 1,964,425 A * | 6/1934 | Bowman | ............ | 33/485 |
| 1,996,553 A * | 4/1935 | Scully | ............ | 33/512 |
| 2,313,920 A * | 3/1943 | Campbell | ............ | 33/484 |
| 2,394,140 A * | 2/1946 | Biscow | ............ | 606/119 |
| 2,694,931 A * | 11/1954 | Handley | ............ | 73/863.31 |
| 3,927,484 A * | 12/1975 | Spiegel et al. | ............ | 40/307 |
| 3,934,351 A * | 1/1976 | Sullivan | ............ | 33/458 |
| 4,118,868 A * | 10/1978 | Johnson | ............ | 33/512 |
| 4,336,087 A * | 6/1982 | Martuch et al. | ............ | 156/85 |
| 4,495,702 A * | 1/1985 | Bergstedt | ............ | 33/512 |
| 6,003,235 A * | 12/1999 | Chen | ............ | 33/512 |
| 6,581,972 B2 * | 6/2003 | Nojima et al. | ............ | 283/81 |
| 7,770,301 B1 * | 8/2010 | Grandberry et al. | ............ | 33/494 |
| 2006/0036232 A1* | 2/2006 | Primavera et al. | ............ | 604/411 |
| 2007/0022617 A1* | 2/2007 | Wilkinson et al. | ............ | 33/542 |
| 2008/0005915 A1* | 1/2008 | Jolin et al. | ............ | 33/493 |

FOREIGN PATENT DOCUMENTS

GB 2150296 A * 6/1985

* cited by examiner

*Primary Examiner* — R. A. Smith

(57) ABSTRACT

A height measuring device and method of measuring height are disclosed. The device includes a first rod having a first opening through a first end of the first rod. The device also includes a second rod having a first opening through a first end of the second rod. The device further includes a first fastener positioned in the first opening of the first rod and the first opening of the second rod. The first fastener engages the first rod and the second rod. In one embodiment each rod includes a shrinkwrap sleeve having measurement markings thereon.

12 Claims, 2 Drawing Sheets

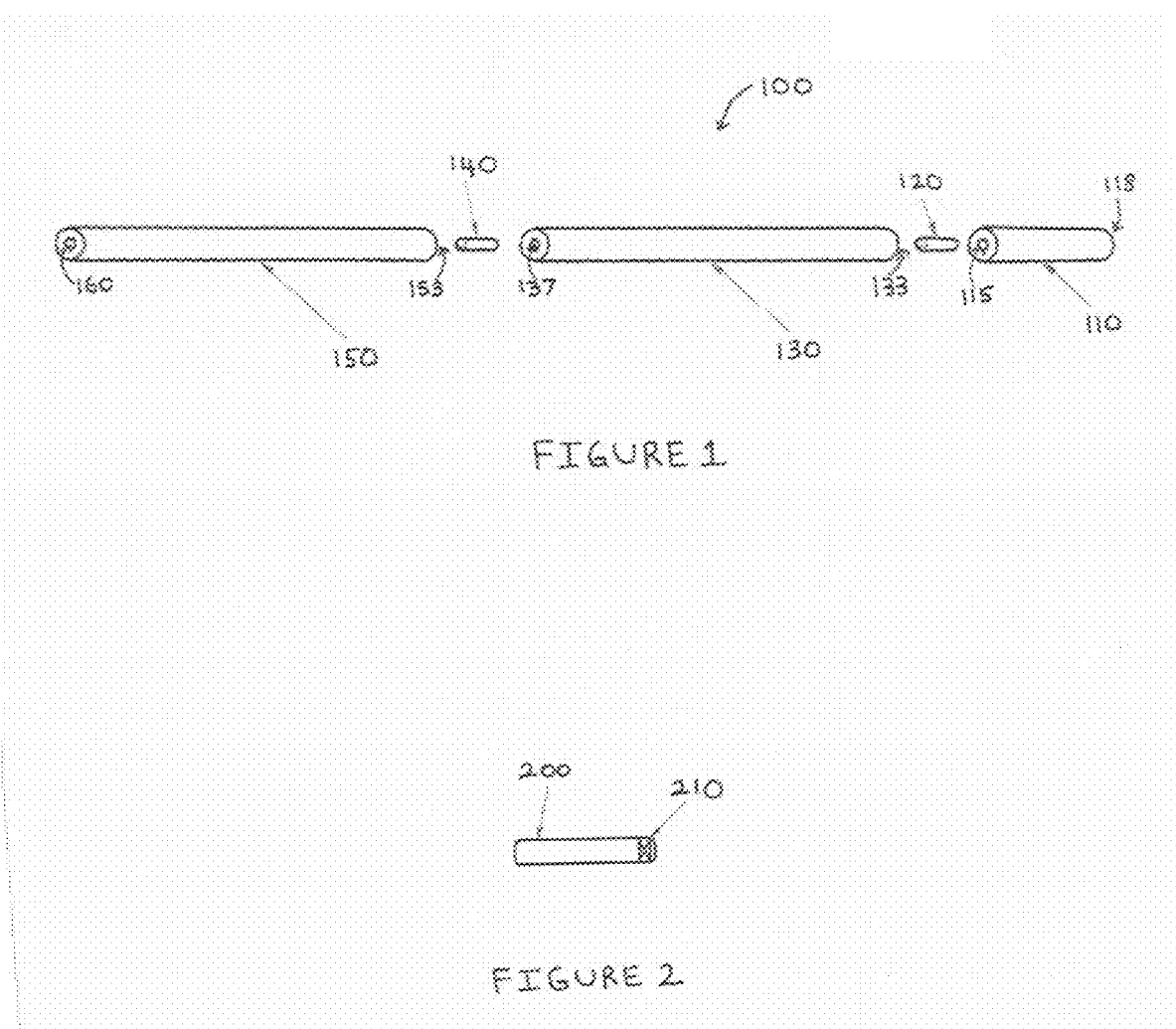

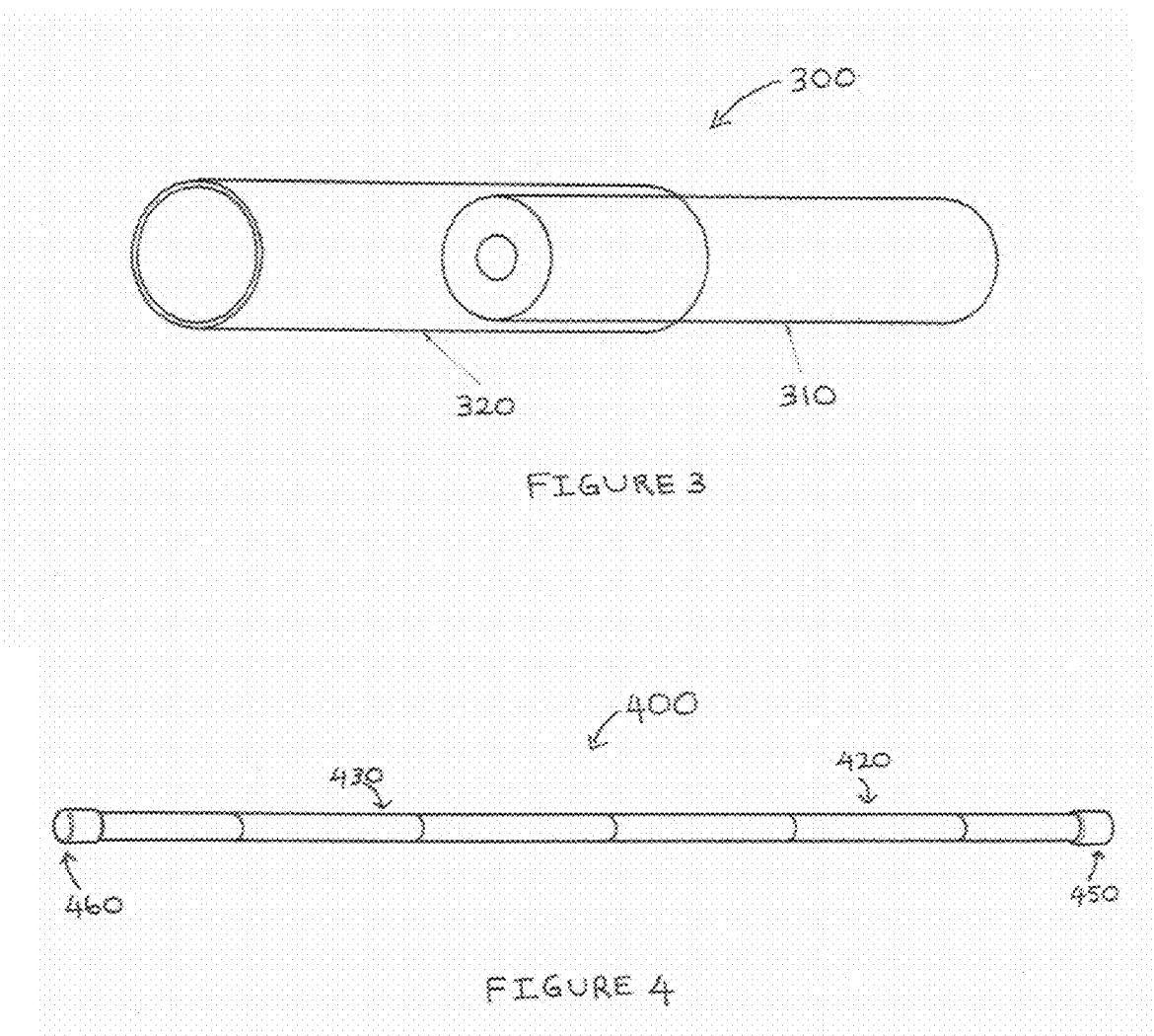

DEVICE FOR MEASURING HEIGHT

FIELD OF THE INVENTION

This invention relates to a height measuring device. More specifically, the invention relates to a height measuring device for measuring height that includes at least one rod and measurement markings.

BACKGROUND OF THE INVENTION

Various methods exist for measuring height, particularly of small children who are growing. Many parents, for example, measure their child's height by having the child stand in front of a door or with their back against the wall and marking a pencil line on the wall, indicating another growth spurt. Some parents use a wall chart against which they monitor their child's growth. Parents can also glue a tape measure or simply paint a narrow board and attach it to the wall, marking inches like a giant yardstick.

When visiting the doctor for a check-up, a child's (or patient's) height is typically measured with a platform type measuring scale on which the patient can stand for measurement of height (and weight). A height measuring rod is attached with it. The platform measuring scales are typically mounted on transport castors to allow free mobility from one place to other.

These methods, while effective for measuring height, would not make suitable gifts for children. What is needed is a height measuring device that can be used and enjoyed throughout childhood and teenage years and that is portable and simple to use.

SUMMARY OF THE INVENTION

The present invention is directed to a height measuring device and method of measuring height. In one embodiment of the present invention, the device comprises a first rod having a first opening through a first end of the first rod. The device also includes a second rod having a first opening through a first end of the second rod. The device further includes a first fastener positioned in the first opening of the first rod and the first opening of the second rod, wherein the first fastener engages the first rod and the second rod. The fastener is selected from the group consisting of a dowel pin, a bolt, a rivet, a screw, a thread, a nail, a clip, and combinations thereof.

In one embodiment of the present invention, the device also includes a first sleeve fitted around the first rod and a second sleeve fitted around the second rod, wherein each sleeve includes measurement markings. The measurement markings are in inches, feet, centimeters, meters, or a combination thereof. The device can also include a first cap coupled to a second end of the first rod. Each rod is formed from a material selected from plastic, polystyrene, polymer, wood, steel, aluminum, fiberglass and combinations thereof The sleeve comprises, but is not limited to, a shrinkwrap material. Alternatively, in place of a sleeve, one or more labels can be placed on the rods and include measurement markings. In another embodiment, paint can be applied to the rods—without any sleeves or labels—and include painted measurement markings on the rods.

In one embodiment of the present invention, the device further comprises a third rod having a first opening through a first end of the third rod; and a second fastener positioned in the first opening of the third rod and a second opening through a second end of the second rod. The second fastener engages the second rod and the third rod. The second fastener is selected from the group consisting of a dowel pin, a bolt, a rivet, a screw, a nail, a clip, and combinations thereof. The device can further comprise a third sleeve fitted around the third rod, wherein the third sleeve includes measurement markings. The device can also include a second cap coupled to a second end of the third rod.

In another embodiment of the present invention, a height measuring device for measuring height is disclosed. The device comprises a first rod having a first opening through a first end of the first rod; a second rod having a first opening through a first end of the second rod and a second opening through a second end of the second rod; a third rod having a first opening through a first end of the third rod; a first fastener positioned in the first opening of the first rod and the first opening of the second rod, the first fastener engaging the first rod and the second rod; and a second fastener positioned in the first opening of the third rod and the second opening of the second rod, the second fastener engaging the second rod and the third rod. The device can further comprise a first sleeve fitted around the first rod, a second sleeve fitted around the second rod, and a third sleeve fitted around the third rod, wherein each sleeve includes measurement markings. The device can also comprise a first cap coupled to a second end of the first rod and a second cap coupled to a second end of the third rod.

In another embodiment of the present invention, a height measuring device for measuring height is disclosed. The device comprises a first rod having a first opening through a first end of the first rod; a second rod having a first opening through a first end of the second rod; a first fastener positioned in the first opening of the first rod and the first opening of the second rod, the first fastener engaging the first rod and the second rod; and a first sleeve fitted around the first rod and a second sleeve fitted around the second rod, wherein each sleeve includes measurement markings. The device can further comprise a third rod having a first opening through a first end of the third rod; a second fastener positioned in the first opening of the third rod and a second opening through a second end of the second rod, the second fastener engaging the second rod and the third rod; and a third sleeve fitted around the third rod, wherein the third sleeve includes measurement markings.

In another embodiment of the present invention, a height measuring device for measuring height is disclosed. The device comprises a rod and a sleeve fitted around the rod, wherein the sleeve includes measurement markings

BRIEF DESCRIPTION OF THE DRAWINGS

FIG. 1 shows a height measuring device for measuring height, in accordance with one embodiment of the present invention.

FIG. 2 shows a fastener for coupling a first rod and a second rod for a height measuring device, in accordance with one embodiment of the present.

FIG. 3 shows a sleeve fitted around a rod for a height measuring device, in accordance with one embodiment of the present invention.

FIG. 4 shows a perspective view of a height measuring device for measuring height, in accordance with one embodiment of the present invention.

DETAILED DESCRIPTION OF THE PREFERRED EMBODIMENTS

FIG. 1 shows a height measuring device 100 for measuring height, in accordance with one embodiment of the present invention. The height measuring device 100 includes a first rod 110 having a first opening 115 through a first end of the first rod 110. The device 100 also includes a second rod 130 having a first opening 133 through a first end of the second rod 130. The device also includes a first fastener 120 that is positioned in the first opening 115 of the first rod 110 and the first opening 133 of the second rod 130. The first fastener 120 engages the first rod 110 and the second 130.

In accordance with another embodiment of the present invention, the device 100 includes a third rod 150 having a first opening 153 through a first end of the third rod 150. The device 100 also includes a second fastener 140 that is positioned in the first opening 153 of the third rod 150 and a second opening 137 through a second end of the second rod 130. The second fastener 140 engages the second rod 130 and the third rod 150.

The rods 110, 130, and 150 are each formed from a material selected from the plastic, polystyrene, polymer, wood, steel, aluminum, fiberglass and combinations thereof. It should be understood that each rod 110, 130, and 150 can be made of any material suitable for a height measuring device. The fasteners 120 and 140 can be a dowel pin, a bolt, a rivet, a screw, a thread, a nail, a clip, and combinations thereof.

The device 100 can also include a first sleeve (not shown in FIG. 1) fitted around the first rod 110 and a second sleeve (not shown in FIG. 1) fitted around the second rod 130. The device 100 or sleeves can include measurement markings (not shown in FIG. 1). The measurement markings can be in inches, feet, centimeters, meters, or combinations thereof The sleeves can be a shrinkwrap material.

Alternatively, in place of a sleeve, one or more labels can be placed on at least one of the rods 110, 130, and 150 and include measurement markings. In another embodiment, paint can be applied to at least one of the rods 110, 130 and 150—without any sleeves or labels—and include painted measurement markings.

In accordance with one embodiment of the present invention, the first rod 110 includes a first cap (not shown in FIG. 1) coupled to a second end 118 of the first rod 110. The third rod 150 can include a second cap (now shown in FIG. 1) coupled to a second end 160 of the third rod 150. The third rod 150 can also include a sleeve (not shown in FIG. 1) fitted around the third rod 150 and that includes measurement markings (not shown in FIG. 1).

FIG. 2 shows a fastener 200 for coupling a first rod and a second rod for a height measuring device, in accordance with one embodiment of the present. As shown in the FIG. 2, an adhesive 210, such as glue, can be applied to an area of the fastener 200 to adhere the fastener 200 to a rod. It should be understood that any adhesive that adheres the fastener 200 to a rod can be used.

FIG. 3 shows a sleeve 320 fitted around a rod 310 for a height measuring device 300, in accordance with one embodiment of the present invention. In one embodiment, heat is applied after the sleeve 320 is fitted around the rod 310. In one embodiment, the sleeve 320 is made of shrinkwrap material.

FIG. 4 shows a perspective view of a height measuring device 400 for measuring height, in accordance with one embodiment of the present invention. The device 400 includes a first rod 420 and a second rod 430. The first rod 420 is coupled to the second rod 430 via a fastener (not shown in FIG. 4). The first rod 420 includes a first cap 450 coupled to an end of the first rod 420. The second rod 430 includes a second cap 460 coupled to an end of the second rod 430.

It should be understood that the height measuring device of the present invention is not limited to any specific number of rods, shapes, sizes, or materials. The rods can be any shape, diameter, or length that allow for the coupling of the rods using a fastener.

Alternatively, in one embodiment, a single rod can be used as a height measuring device. In this embodiment, a sleeve is fitted around the rod, wherein the sleeve includes measurement markings.

In one embodiment, the height measuring device of the present invention is a detachable device. That is, the rods can be detached from one another and re-coupled as necessary.

The following is one example of manufacturing a height measuring device, in accordance with one embodiment of the present invention. A hole, from about ¼ inches to about ¾ inches, is drilled through a first end of a first rod, through a first end and a second end of a second rod, and through a first end of a third rod. A first rod sleeve is positioned around the first rod. A second rod sleeve is positioned around the second rod and a third rod sleeve is positioned around the third rod. Heat is applied to each sleeve. Adhesive glue is applied to a first area of a first fastener. The glued first fastener is inserted through a hole at the first end of the first rod. In some cases, light tapping with a hammer may be required in order to insert the first fastener through the hole. Adhesive glue is applied again to a second area of the first fastener that is protruding from the first end of the first rod and that will be inserted into a first end of the second rod. The first fastener couples the first rod and the second rod. Thus, the first rod and the second rod couple to form one rod.

Still referring to the example above of manufacturing a height measuring device, adhesive glue is applied to a first area of a second fastener. The glued second fastener is inserted through a hole at the second end of the second rod. In some cases, a light tapping with a hammer may be required in order to insert the second fastener through the hole. Adhesive glue is applied again to a second area of the second fastener that is protruding from the second end of the second rod and that will be inserted into a first end of the third rod. The second fastener couples the second rod and the third rod. At this point, the first rod, the second rod, and the third rod couple to form one rod. Measurement markings, located on each sleeve, can be properly aligned by twisting the coupled rods as needed. A first cap can be applied to a second end of the first rod—the end of the first rod that is not connected to the second rod. A second cap can be applied to a second end of the third rod—the end of the third rod that is not connected to the second rod.

The present invention has been described in terms of specific embodiments incorporating details to facilitate the understanding of principles of constriction and operation of the invention. Such reference herein to specific embodiments and details thereof is not intended to limit the scope of the claims appended hereto. It will be apparent to those skilled in the art that modification may be made in the embodiments chosen for illustration without departing from the spirit and scope of the invention

What is claimed is:

1. A height measuring device for measuring height comprising:
   a. a first rod having a first opening through a first end of the first rod;
   b. a second rod having a first opening through a first end of the second rod;
   c. a first fastener positioned in the first opening of the first rod and the first opening of the second rod, the first fastener engaging the first rod and the second rod; and
   d. a first sleeve fitted around the first rod and a second sleeve fitted around the second rod, wherein each sleeve includes measurement markings, and wherein each sleeve is made of a shrinkwrap material.

2. The device of claim 1 further comprising a first cap coupled to a second end of the first rod.

3. The device of claim 1 wherein each rod is formed from a material selected from the group consisting of plastic, polystyrene, polymer, wood, steel, aluminum, fiberglass and combinations thereof.

4. The device of claim 1 wherein the measurement markings are in inches, feet, centimeters, meters, or a combination thereof.

5. The device of claim 1 wherein the first fastener is selected from the group consisting of a dowel pin, a bolt, a rivet, a screw, a thread, a nail, a clip, and combinations thereof.

6. The device of claim 1 further comprising:
   a. a third rod having a first opening through a first end of the third rod; and
   b. a second fastener positioned in the first opening of the third rod and a second opening through a second end of the second rod, the second fastener engaging the second rod and the third rod.

7. The device of claim 6 further comprising a third sleeve fitted around the third rod, wherein the third sleeve includes measurement markings.

8. The device of claim 6 further comprising a second cap coupled to a second end of the third rod.

9. The device of claim 6 wherein the second fastener is selected from the group consisting of a dowel pin, a bolt, a rivet, a screw, a thread, a nail, a clip, and combinations thereof.

10. The device of claim 9 wherein adhesive glue is applied to the first fastener prior to engaging the first rod and the second rod and applied to the second fastener prior to engaging the second rod and the third rod.

11. The device of claim 1 further comprising one or more labels placed on at least one of the first rod and the second rod, wherein the one or more labels include measurement markings.

12. The device of claim 1 wherein paint is applied to the first rod and the second rod, wherein each rod includes painted measurement markings.

* * * * *